(12) United States Patent
Diaz et al.

(10) Patent No.: US 11,104,870 B1
(45) Date of Patent: Aug. 31, 2021

(54) AUTOMATIC FLUSH ACTIVATED TOILET ODOR PREVENTION TABLET

(71) Applicants: Jonathan Diaz, Poughkeepsie, NY (US); Daniel Quintana, New Paltz, NY (US)

(72) Inventors: Jonathan Diaz, Poughkeepsie, NY (US); Daniel Quintana, New Paltz, NY (US)

( * ) Notice: Subject to any disclaimer, the term of this patent is extended or adjusted under 35 U.S.C. 154(b) by 0 days.

(21) Appl. No.: 16/837,860

(22) Filed: Apr. 1, 2020

(51) Int. Cl.
| | | |
|---|---|---|
| *C11D 1/04* | (2006.01) | |
| *C11D 3/50* | (2006.01) | |
| *C11D 3/04* | (2006.01) | |
| *C11D 17/00* | (2006.01) | |
| *A61L 9/05* | (2006.01) | |
| *E03D 9/02* | (2006.01) | |
| *C11D 3/38* | (2006.01) | |
| *C11D 1/32* | (2006.01) | |
| *C11D 3/20* | (2006.01) | |
| *C11D 1/36* | (2006.01) | |

(52) U.S. Cl.
CPC ............ *C11D 17/0056* (2013.01); *A61L 9/05* (2013.01); *C11D 1/32* (2013.01); *C11D 1/36* (2013.01); *C11D 3/2065* (2013.01); *C11D 3/2079* (2013.01); *C11D 3/38* (2013.01); *C11D 3/50* (2013.01); *C11D 17/0073* (2013.01); *E03D 9/02* (2013.01); *E03D 2009/024* (2013.01)

(58) Field of Classification Search
CPC ........... C11D 1/32; C11D 1/36; C11D 3/2079; C11D 3/2065; C11D 3/38; C11D 3/50; C11D 17/0056

USPC ........ 510/101, 191, 192, 446, 447, 477, 488, 510/505, 506
See application file for complete search history.

(56) References Cited

U.S. PATENT DOCUMENTS

| | | | | |
|---|---|---|---|---|
| 4,165,293 | A * | 8/1979 | Gordon ............. | C11D 17/0095 510/147 |
| 6,151,722 | A | 11/2000 | Lubrano | |
| 6,387,321 | B1 | 5/2002 | McGill | |
| 6,861,397 | B2 * | 3/2005 | Seitz, Jr. ................. | C11D 3/48 510/119 |
| 7,015,179 | B1 * | 3/2006 | Massaro ............. | C11D 3/2072 510/101 |
| 7,908,680 | B2 | 3/2011 | Akitsu | |
| 8,367,595 | B2 * | 2/2013 | Cheung ................ | C11D 3/3776 510/191 |

(Continued)

OTHER PUBLICATIONS https://www.homedepot.com/p/Ty-D-Bol-1-7-oz-Toilet-Bowl-Cleaner-Lavender-Scent-Tablet-6-Pack-591000-6T/206742601.
https://www.kickstarter.com/projects/1868936202/looloo-worlds-first-automatic-on-the-toilet-freshe.

*Primary Examiner* — Gregory R Delcotto
(74) *Attorney, Agent, or Firm* — Saile Ackerman LLC; Stephen B. Ackerman

(57) ABSTRACT

A toilet odor prevention tablet and method for automatic flush activation is described, where the toilet odor prevention tablet includes one or more of a plurality of plant-based oils, glycerine, a solid carrier, and one or more of a plurality of essential oils. The method of use for automatic flush activation includes providing a toilet odor prevention tablet, including all natural ingredients, and depositing the toilet bowl odor prevention tablet directly into a toilet tank, where placement of the tablet results in a film that reduces an odor emitting capacity of human excrement and delivers a fresh layer of odor prevention with every flush of a toilet.

18 Claims, 4 Drawing Sheets

(56) References Cited

U.S. PATENT DOCUMENTS

| | | | |
|---|---|---|---|
| 8,966,674 B2* | 3/2015 | Lu | C11D 17/0056 |
| | | | 4/223 |
| 9,724,445 B2 | 8/2017 | Rabin et al. | |
| 2001/0025020 A1* | 9/2001 | Holderbaum | C11D 17/0078 |
| | | | 510/446 |
| 2003/0040459 A1* | 2/2003 | Araya | C11D 3/124 |
| | | | 510/446 |
| 2003/0134762 A1* | 7/2003 | Finucane | C11D 3/2075 |
| | | | 510/141 |
| 2003/0166489 A1* | 9/2003 | Van Asten | C11D 17/0073 |
| | | | 510/440 |
| 2003/0199405 A1* | 10/2003 | Abbas | A61Q 1/10 |
| | | | 510/141 |
| 2004/0128751 A1 | 7/2004 | Haq | |
| 2005/0124515 A1* | 6/2005 | Ospinal | C11D 3/2065 |
| | | | 510/156 |
| 2006/0135385 A1* | 6/2006 | Massaro | C11D 3/2072 |
| | | | 510/141 |
| 2010/0235975 A1* | 9/2010 | Cheung | E03D 9/02 |
| | | | 4/222 |
| 2010/0256031 A1* | 10/2010 | Wu | A61Q 19/008 |
| | | | 510/130 |
| 2010/0299818 A1* | 12/2010 | Lu | C11D 17/0056 |
| | | | 4/223 |
| 2011/0142784 A1* | 6/2011 | Leipold | C11D 3/3723 |
| | | | 424/76.7 |
| 2014/0378363 A1* | 12/2014 | Thiessies | C11D 10/04 |
| | | | 510/151 |
| 2016/0000094 A1* | 1/2016 | Modak | A01N 31/02 |
| | | | 424/736 |
| 2017/0071214 A1* | 3/2017 | Rehage | A01N 59/06 |
| 2017/0252293 A1* | 9/2017 | Brumbaugh | A61Q 19/007 |
| 2018/0148674 A1* | 5/2018 | Khamis | C11D 17/04 |
| 2018/0155908 A1* | 6/2018 | Reichert | E03D 9/02 |

\* cited by examiner

| 500 | Week | Subject | Before | After | During | 3rd Party |
|---|---|---|---|---|---|---|
| Tester 1 (510) | Week 1 | Tester 1 | 0 | 1 | 0 | 0 |
| | Week 2 | Tester 1 | 0 | 1 | 0 | 0 |
| | Week 3 | Tester 1 | 0 | 1 | 0 | 0 |
| | Week 4 | Tester 1 | 0 | 1 | 0 | 0 |
| Tester 2 (520) | Week 1 | Tester 2 | 0 | 1 | 0 | 0 |
| | Week 2 | Tester 2 | 0 | 1 | 0 | 0 |
| | Week 3 | Tester 2 | 0 | 2 | 1 | 0 |
| | Week 4 | Tester 2 | 0 | 2 | 1 | 1 |
| Tester 3 (530) | Week 1 | Tester 3 | 0 | 0 | 0 | 0 |
| | Week 2 | Tester 3 | 0 | 1 | 0 | 0 |
| | Week 3 | Tester 3 | 0 | 1 | 0 | 0 |
| | Week 4 | Tester 3 | 0 | 2 | 1 | 0 |

FIG. 5

AUTOMATIC FLUSH ACTIVATED TOILET ODOR PREVENTION TABLET

FIELD

The present disclosure relates generally to a toilet odor prevention tablet. More particularly, the present invention relates to a toilet odor prevention tablet comprised of all natural ingredients.

BACKGROUND

The odor produced in toilets during the excretion of fecal material from the human body is often offensive. The offensive odors diffuse through the toilet water and into the atmosphere of the toilet environment. One popular current practice is to use a small spray bottle, just prior to toilet use, to deliver a combination of oils and coagulants to create a thin barrier at the surface of toilet water in order to trap odors created by the human excrement.

SUMMARY

Accordingly, it is an object of one or more embodiments of the present disclosure to provide a toilet odor prevention tablet that converts toilet water into a solution that reduces the odor emitting capacity of human excrement.

It is a further object of one or more embodiments of the disclosure to provide toilet odor prevention with all natural ingredients.

Still further, it is an object of one or more embodiments of the disclosure to provide a toilet odor prevention tablet that releases essential oils and glycerine.

Still further, it is an object of one or more embodiments of the disclosure to deliver a fresh layer of odor prevention with every flush of the toilet.

Other objects will appear hereinafter.

The above and other objects of the present disclosure may be accomplished in the following manner. The present disclosure proposes a toilet bowl odor prevention tablet, comprising one or more of a plurality of plant-based oils, glycerine, a solid carrier, and one or more of a plurality of essential oils. One way to manufacture the toilet bowl odor prevention tablet is to start with a melt and pour soap base, which are commonly available to consumers who wish to make their own bars of soap. The starting point is typically a block, which is melted and then poured into a mold. One ingredient that is required for the disclosed tablet is glycerine. This may be found already in the melt and pour soap base, or if absent, needs to be added. One or more essential oils are added to the poured soap base, before it hardens. Some soap bases are honey-based, which is preferred for the disclosed tablet.

The above and other objects of the present disclosure may be further accomplished with a method of use for automatic flush activated toilet odor prevention. The steps include providing a toilet odor prevention tablet, including all natural ingredients. The steps also include depositing the toilet bowl odor prevention tablet directly into a toilet tank, where the tablet converts toilet water into a solution that reduces an odor emitting capacity of human excrement and delivers a fresh layer of odor prevention with every flush of a toilet.

In various embodiments, the toilet bowl odor prevention tablet sits in a bracket attached to the toilet tank.

BRIEF DESCRIPTION OF THE DRAWINGS

The present disclosure will be more clearly understood from the following description taken in conjunction with the accompanying drawings in which like reference numerals designate similar or corresponding elements, regions and portions and in which:

FIG. 5 shows test results in use of the toilet bowl odor prevention tablet of the present disclosure.

DETAILED DESCRIPTION

Figure 1:
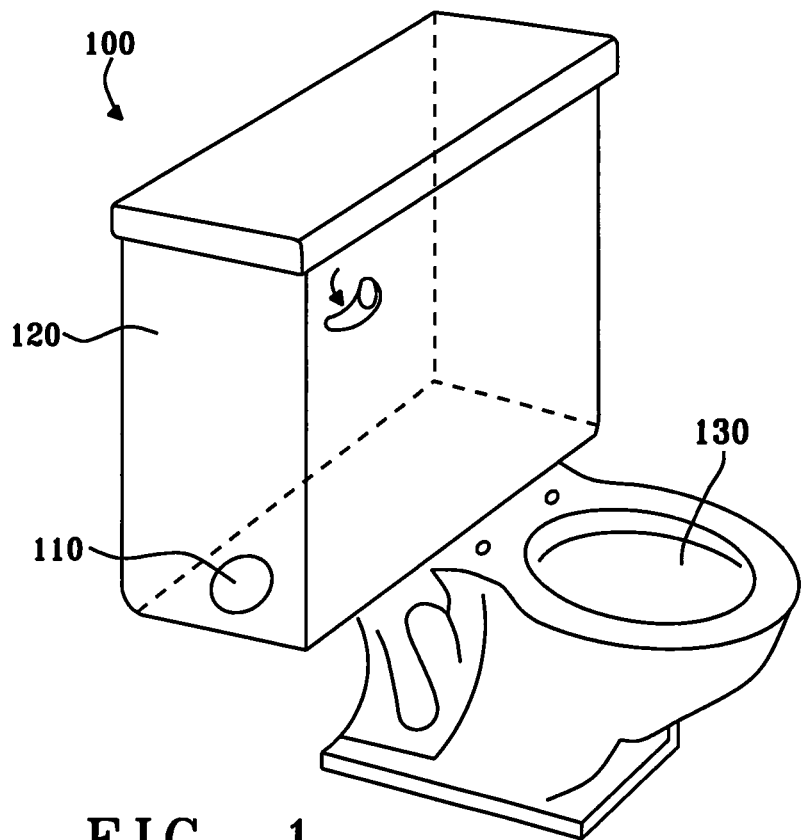
FIG. 1 shows an exemplary embodiment, where the disclosed toilet bowl odor prevention tablet is dropped directly into a toilet tank.

The present disclosure proposes a toilet bowl odor prevention tablet, comprising one or more of a plurality of plant-based oils, glycerine, a solid carrier, and one or more of a plurality of essential oils. The primary active ingredients that are released once the tablet is placed in the toilet tank, are the essential oil(s) and glycerine. The essential oil(s) provide a scent, and the glycerine is the primary ingredient that forms a film or barrier on the surface of the water in the toilet bowl. The carrier stays in a solid form and is not active. The resulting toilet water solution reduces the odor emitting capacity of human excrement, and odor prevention is delivered with every flush.

One or more essential oils are used, to provide a pleasant scent to the toilet water and surroundings, after each flush. During manufacture of the tablets, the amounts noted in the following are based on a number of drops from a standard dropper used to dispense such oils. A minimum of about 200 drops of the essential oils(s) are believed necessary to provide the minimum scent. It is also believed that a maximum of about 1000 drops be used, as over that amount would likely not provide any more scent or could lead to the scent being overpoweringly strong.

Essential oils used could include, but are not limited to, lemon, bergamot, and/or orange essential oils. A preferred embodiment includes about 250 drops of lemon essential oil, about 100 drops of bergamot essential oil, and about 150 drops of orange essential oil. Other combinations—such as less than these 3 essential oils, varying the relative proportion of each essential oil, and using other essential oils in combination—could be used.

Depending on the essential oil(s) used, the tablet has an initial, non-white color. For example, the use of orange and lemon oils will give the tablet an orange or orange-yellow color. Once the tablet has lost some or all of its effectiveness, it will turn to a white color, which can be used as a visual indicator to the consumer that the tablet is no longer effective and should be changed.

Glycerine is another important ingredient for the disclosed tablet. Some pour and melt soap bases come with glycerine already included in the product. Where glycerine is not included, it needs to be added, with the range of glycerine used between about 5 and 20 teaspoons. Preferably, about 10 teaspoons are used.

One way to manufacture the toilet bowl odor prevention tablet is to start with a melt and pour soap base, which are commonly available to consumers who wish to make their own bars of soap. The starting point is typically a block, which is melted and then poured into a mold. One ingredient that is required for the disclosed tablet is glycerine. This may be found already in the melt and pour soap base, or if absent, needs to be added. One or more essential oils are added to the poured soap base, before it hardens. Some soap bases are honey-based, which is preferred for the disclosed tablet. The quantities of essential oils and glycerine noted above are for an exemplary cylindrical tablet having dimensions of about 2.5" in diameter, and about 0.75" thick. A larger or smaller tablet could be made with the amounts of essential oils and glycerine adjusted accordingly, and proportionally.

The solid carrier includes, preferably, honey, water, a saponifying agent, sorbitol, a penetration enhancer, an emulsifier and a conditioner. The saponifying agent is preferably sodium hydroxide, though other saponifying agents could alternately be used. The penetration enhancer is preferably propylene glycol, though other penetration enhancers could alternately be used. The emulsifier is preferably sorbitan oleate, though other emulsifiers could alternately be used. The conditioner is preferably oat protein, though other conditioners could alternately be used. The purpose of the solid carrier is primarily to act as a carrier for the essential oil blend, and the glycerine, which acts as a thickening agent for the odor prevention barrier.

FIG. 1 shows 100, an exemplary embodiment, where a toilet bowl odor prevention tablet is dropped directly into a toilet tank. A representative toilet tank 120 contains toilet bowl odor prevention tablet 110 of the present disclosure, dropped into the tank. Each flush of the toilet causes the tablet to partially dissolve in the water, delivering odor prevention to the top surface of the water in the toilet bowl 130, via a thin film that forms on the water's surface. This film forms immediately, within about one minute, after the water in the bowl has completed being replenished after a flush cycle. The tablet lasts for approximately 4 weeks, or approximately 300-500 flushes.

Figure 2A:
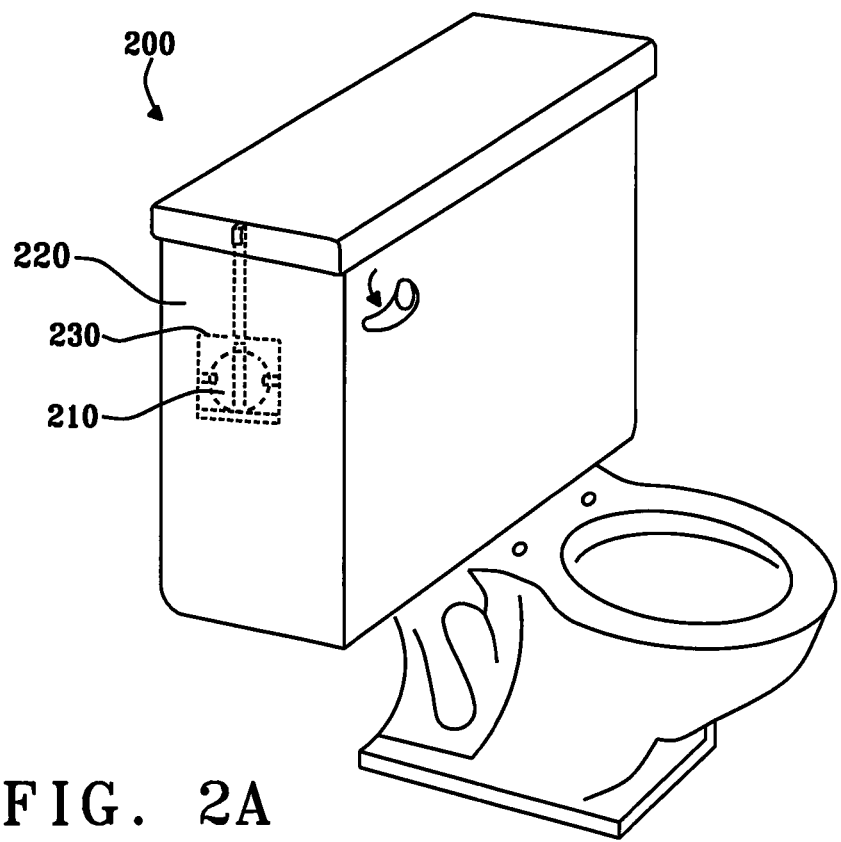
FIG. 2A shows the toilet bowl odor prevention tablet sitting in a bracket of the present disclosure, attached to the side of a toilet tank.

It may be desirable to have the disclosed tablet suspended above the bottom of the tank 120. This could be accomplished in a variety of ways. In one embodiment, FIG. 2A shows 200, the toilet bowl odor prevention tablet as disclosed sitting in a bracket, attached to the side of a toilet tank. The bracket is long enough so that the tablet is submerged in the tank water. Referring to FIG. 2A, bracket 230 holds toilet bowl odor prevention tablet 210 and attaches to a side of toilet tank 220.

Figure 2B:
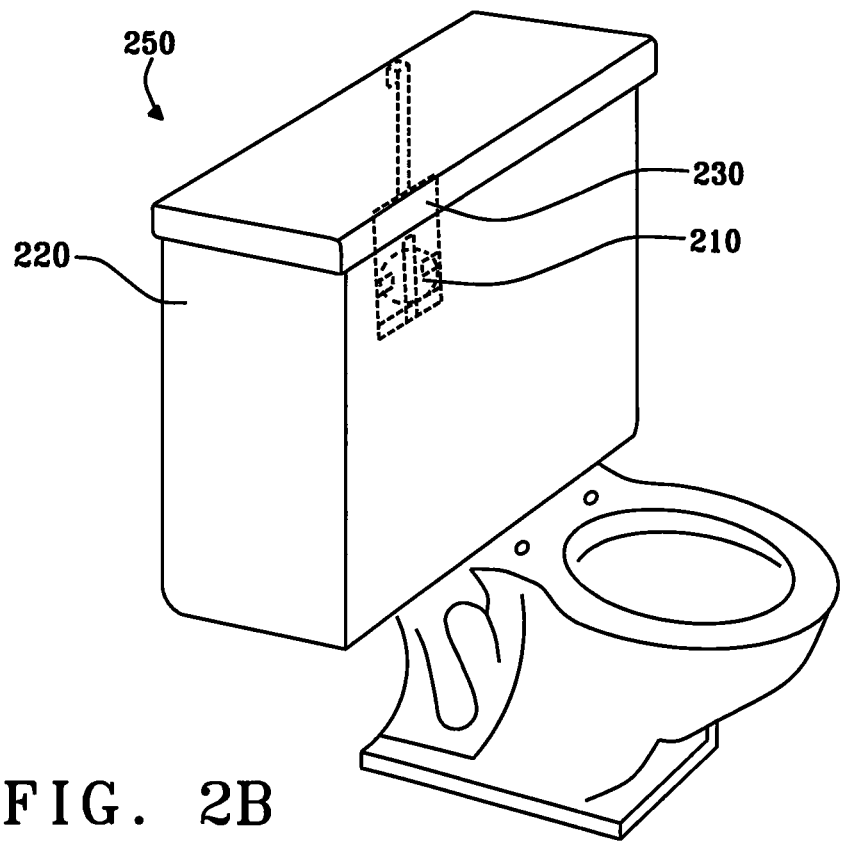
FIG. 2B shows the toilet bowl odor prevention tablet sitting in the bracket of the present disclosure, attached to the back of a toilet tank.

FIG. 2B shows 250, a toilet bowl odor prevention tablet sitting in a bracket, alternatively attached to the back of a toilet tank. Referring to FIG. 2B, bracket 230 holds toilet bowl odor prevention tablet 210 and attaches to the back of toilet tank 220.

Figure 3A:
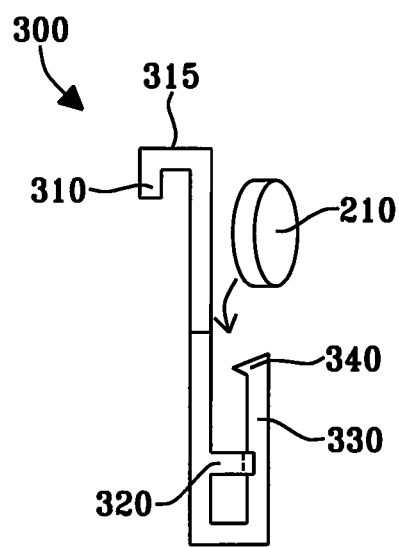
FIG. 3A shows a side view of a bracket comprising a hanger and three tabs, of the present disclosure.

FIG. 3A shows 300, a side view of a bracket comprising a hanger and three tabs, of the present disclosure. The hanger is configured to attach to a side or a back of a toilet tank, shown in FIGS. 2A and 2B, respectively, in which the hanger portion 315 rests on the top edge of the tank 220, and has an overhanging section 310. Tabs 320 and 330 are configured to hold and clip toilet bowl odor prevention tablet 210 in place, where tab 330 has a notch 340 at its upper end. Note that the body of the bracket is slightly larger than the tablet.

Figure 3B:
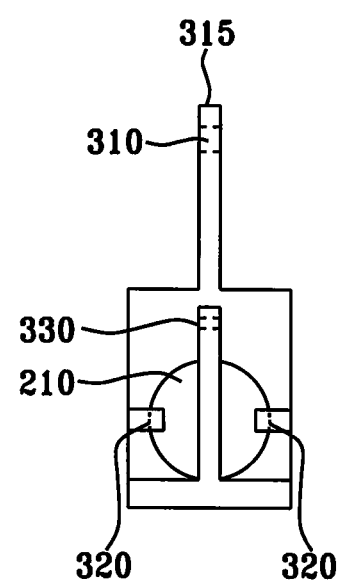
FIG. 3B shows a front view of a bracket comprising a hanger and three tabs, of the present disclosure.

FIG. 3B is a front view of a bracket comprising the hanger tabs, of the present disclosure. The two tabs 320 are preferably formed on either side of the body of the bracket, and are preferably shorter than the front tab 330. The tabs keep tablet 210 from sliding out of the bracket.

Figure 3C:
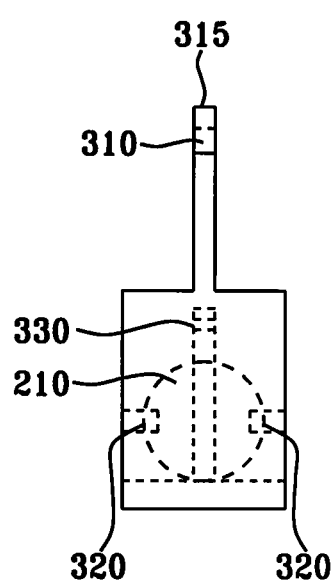
FIG. 3C shows a back view of the bracket comprising a hanger and three tabs, of the present disclosure.

FIG. 3C is a back view of the bracket 300. The bracket is constructed of plastic, or recycled plastic material, or any other material that would not be affected by remaining in water in the toilet tank.

Figure 4:
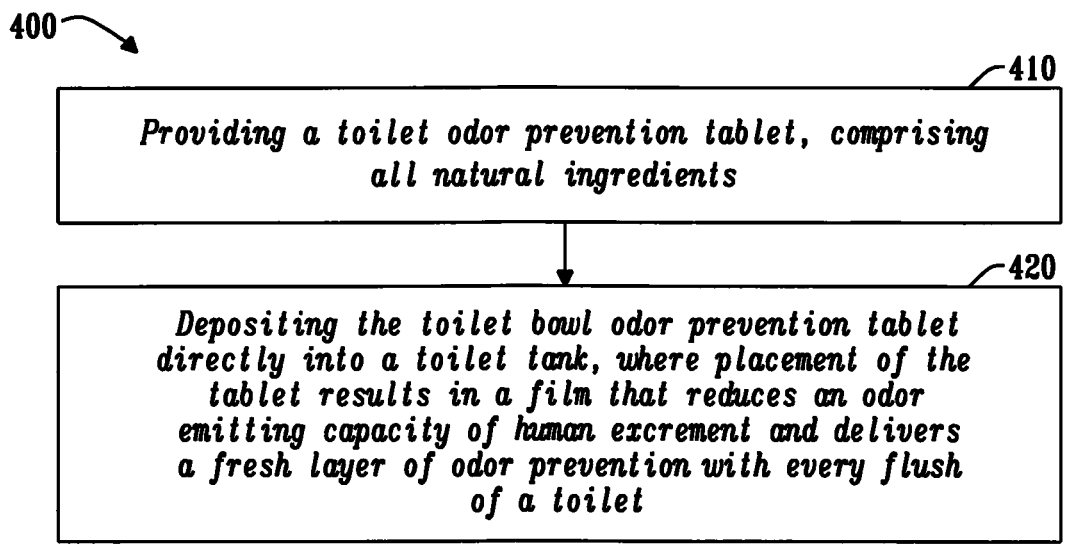
FIG. 4 is a flow chart of a method of use for automatic flush activated toilet odor prevention.

FIG. 4 is flow chart 400, of a method of use for automatic flush activated toilet odor prevention. The steps include 410, providing a toilet odor prevention tablet, including all natural ingredients. The steps also include 420, depositing the toilet bowl odor prevention tablet directly into a toilet tank, where the tablet converts toilet water into a solution that reduces an odor emitting capacity of human excrement and delivers a fresh layer of odor prevention with every flush of a toilet.

Test Results

To test the effectiveness of the toilet bowl odor prevention tablet, an experiment was performed using a tablet made of the following ingredients: coconut oil, palm oil, safflower oil, glycerine, honey, purified water, sodium hydroxide, sorbitol, propylene glycol, sorbitan oleate, oat protein, 250 drops of Lemon Essential Oil, 100 drops of Bergamot Essential Oil, and 150 drops of Orange Essential Oil. The circular tablet size used for the experiment was 2.5" in diameter and 0.75" thick.

The tablet was dropped into the toilet tank, and 3 minutes were allowed to pass. The toilet was flushed to activate the tablet immediately prior to bowel excretion, the bowel contents were excreted, and then the toilet was flushed again. Observations were made to smell and detect the extent of bowel odor and scent odor. One observation was made before the bowel excretion process, and two observations were made during a 1-3 minute period immediately after completing the excretion process. A first after-use observation was made before leaving the bathroom or toilet area, and a last after-use observation was made after leaving the bathroom for 1-3 minutes and then returning. Testers also found a third party non-user to make one observation during the 1-3 minute after use period. The test scale for each observation was 0-10 with 0 indicating no odor and 10 indicating an extremely bad odor. A numeric range of smell when no tablet is used would typically be in the 7-9 range.

FIG. 5 shows 500, test observations of three independent testers and third parties, for use of the toilet bowl odor prevention tablet of the present disclosure. The testing was performed once a week over a 4-week period, during which a single tablet of the disclosure was in use in each toilet tank for the duration of the testing. Note that in 510, Tester 1 observed an odor of 1 during the 1-3 minute period immediately after completing the excretion process, and an odor of 0 after leaving the bathroom for 1-3 minutes and then returning, in all four weeks of use. Tester 1's third party non-user observed an odor of 0 during the 1-3 minute after use period, in all four weeks of use. In 520, Tester 2 observed an odor of 1 during the first two weeks of use in the 1-3 minute period immediately after completing the excretion process, and an odor of 2 during the last two weeks of use in the 1-3 minute period immediately after completing the excretion process. Tester 2 observed an odor of 0 during the first two weeks of use after leaving the bathroom for 1-3 minutes and then returning, and an odor of 1 during the last two weeks of use after leaving the bathroom for 1-3 minutes. Tester 2's third party non-user observed an odor of 0 during the first three weeks of the 1-3 minute after use period, and an odor of 1 during the last week of the 1-3 minute after use period. In 530, Tester 3 observed an odor of 0 during the first week of use in the 1-3 minute period immediately after completing the excretion process, an odor of 1 during the second and third week of use in the 1-3 minute period immediately after completing the excretion process, and an odor of 2 during the last week of use in the 1-3 minute period immediately after completing the excretion process. Tester 3 observed an odor of 0 during the first three weeks of use after leaving the bathroom for 1-3 minutes and then returning, and an odor of 1 during the last week of use after leaving the bathroom for 1-3 minutes. Tester 3's third party non-user observed an odor of 0 during the 1-3 minute after use period, in the four weeks of use. From the experimental results shown in FIG. 5, it can be seen that the toilet odor prevention tablet is effective during the 1-3 minute period immediately after completing the excretion process, as shown by odors in the 0 to 2 range, and is also effective after leaving the bathroom for 1-3 minutes and then returning, for both the Test and third party non-user, as shown by odors in the 0 to 1 range.

The main advantage of one or more embodiments of the present disclosure include eliminating unwanted odors in a toilet area during and after excretion of fecal material. Another advantage, as compared to the popular spray product approach, is eliminating the need to remember to spray an odor prevention spray before sitting on the toilet, and eliminating the need to get close to the toilet bowl to apply the spray. The odor prevention tablet of the invention can be simply dropped into the toilet tank or set in a toilet tank bracket, to eliminate odors with every flush of the toilet. It will maintain this capability even if the toilet is not flushed for a day or a few days or even longer.

While particular embodiments of the present disclosure have been illustrated and described, it will be understood by those skilled in the art that various changes in form and details may be made without departing from the spirit and scope of the invention.

What is claimed is:

1. A toilet bowl odor prevention tablet, comprising:
   one or more of a plurality of plant-based oils;
   glycerine, configured to form a film or barrier on the surface of the water in the toilet bowl, and to act as a thickening agent for an odor prevention barrier;
   one or more essential oils, configured to provide a scent for the odor prevention barrier and an orange or orange-yellow color for said toilet bowl odor prevention tablet; and
   a solid carrier, configured to act as a carrier for the one or more essential oils and to result in a white solid form to indicate an end point of effectiveness for the odor prevention tablet after the essential oils are removed.

2. The toilet bowl odor prevention tablet of claim 1, wherein said one or more of a plurality of plant-based oils comprise coconut, palm, and/or safflower oil.

3. The toilet bowl odor prevention tablet of claim 1, wherein said solid carrier comprises honey.

4. The toilet bowl odor prevention tablet of claim 3, wherein said solid carrier further comprises water, a saponifying agent, sorbitol, and an emulsifier.

5. The toilet bowl odor prevention tablet of claim 3, wherein said solid carrier further comprises a conditioner.

6. The toilet bowl odor prevention tablet of claim 4, wherein said saponifying agent comprises sodium hydroxide.

7. The toilet bowl odor prevention tablet of claim 4, wherein said emulsifier comprises sorbitan oleate.

8. The toilet bowl odor prevention tablet of claim 5, wherein said conditioner comprises oat protein.

9. The toilet bowl odor prevention tablet of claim 1, wherein said solid carrier further comprises a penetration enhancer, and wherein said penetration enhancer is propylene glycol.

10. The toilet bowl odor prevention tablet of claim 1, wherein said one or more of a plurality of essential oils comprises lemon, bergamot, and/or orange essential oils.

11. The toilet bowl odor prevention tablet of claim 1, comprising a range of glycerine between about 5 and 20 teaspoons.

12. The toilet bowl odor prevention tablet of claim 1, wherein said tablet lasts for approximately 4 weeks, or between about 300 and 500 flushes, before needing to be replaced.

13. The toilet bowl odor prevention tablet of claim 1, further comprising a bracket, comprising:
   a hanger, configured to attach to a side or a back of a toilet tank; and
   three tabs, configured to hold a toilet bowl odor prevention tablet.

14. The toilet bowl odor prevention tablet of claim 13, wherein a body of said bracket is slightly larger than said toilet bowl odor prevention tablet itself.

15. The toilet bowl odor prevention tablet of claim 14, wherein said three tabs comprise two tabs on either side of said body, and one front tab notched at its top.

16. A method of use for automatic flush activated toilet odor prevention, comprising:
   providing the toilet odor prevention tablet according to claim 1; and
   depositing said toilet bowl odor prevention tablet directly into a toilet tank; wherein placement of said tablet results in a film that reduces an odor emitting capacity of human excrement and delivers a fresh layer of odor prevention with every flush of a toilet.

17. The method of claim 16, wherein said depositing said toilet bowl odor prevention further comprises:
   inserting said toilet bowl odor prevention tablet into a bracket; and
   positioning said bracket on to an inner portion of said toilet tank.

18. The method of claim 16, wherein said toilet odor prevention tablet lasts for approximately 4 weeks, or 300 to 500 flushes, before needing to be replaced.

* * * * *